(12) United States Patent
Salo

(10) Patent No.: US 7,619,723 B2
(45) Date of Patent: Nov. 17, 2009

(54) REFRACTOMETER

(75) Inventor: Harri J. Salo, Vantaa (FI)

(73) Assignee: Janesko Oy, Vantaa (FI)

( * ) Notice: Subject to any disclaimer, the term of this patent is extended or adjusted under 35 U.S.C. 154(b) by 402 days.

(21) Appl. No.: 11/501,827

(22) Filed: Aug. 10, 2006

(65) Prior Publication Data

US 2007/0052949 A1   Mar. 8, 2007

(30) Foreign Application Priority Data

Aug. 12, 2005   (FI) .................................. 20055434

(51) Int. Cl.
*G01N 21/41*   (2006.01)

(52) U.S. Cl. ...................... 356/128; 356/135

(58) Field of Classification Search ........................ None
See application file for complete search history.

(56) References Cited

U.S. PATENT DOCUMENTS

| | | | |
|---|---|---|---|
| 2,445,499 A | | 7/1948 | Silge |
| 2,556,344 A | | 6/1951 | Silge |
| 3,487,069 A | * | 12/1969 | Maselli ........................ 356/135 |
| 4,422,714 A | * | 12/1983 | Benoit et al. ................. 356/136 |
| 4,692,024 A | * | 9/1987 | Bloss .......................... 356/135 |
| 4,940,328 A | * | 7/1990 | Hartman ...................... 356/481 |
| 4,997,278 A | * | 3/1991 | Finlan et al. ................. 356/128 |
| 5,223,142 A | * | 6/1993 | Kolbert ....................... 356/128 |
| 5,565,978 A | * | 10/1996 | Okubo et al. ................ 356/128 |
| 5,596,320 A | * | 1/1997 | Barnes ........................ 356/136 |
| 5,973,774 A | * | 10/1999 | Haggett et al. .............. 356/135 |
| 6,690,452 B2 | * | 2/2004 | Wilks, Jr. .................... 356/436 |
| 7,064,816 B2 | * | 6/2006 | Langenbacher et al. ..... 356/128 |
| 7,221,440 B2 | * | 5/2007 | McCann et al. ............. 356/128 |
| 2004/0145730 A1 | | 7/2004 | Mahrt et al. |

FOREIGN PATENT DOCUMENTS

| | | |
|---|---|---|
| DE | 758908 C | 10/1942 |
| FI | 108259 B | 12/2001 |
| FI | 113566 B | 5/2004 |
| JP | 63-071637 A | 4/1988 |

OTHER PUBLICATIONS

Finnish Official Action dated Aug. 8, 2006.

\* cited by examiner

*Primary Examiner*—Michael A Lyons
*Assistant Examiner*—Juan D Valentin
(74) *Attorney, Agent, or Firm*—Buchanan Ingersoll & Rooney PC

(57) ABSTRACT

A refractometer is disclosed having a light source and an optical window to be positioned in a process liquid. A beam of rays is directed from the light source to an interface (RP) between the process liquid and the optical window and leading back part of the beam of rays refracted from the interface to the inside of the optical window. An image formed in the above manner is observed. The beam of rays from the light source is directed to the interface (RP) between the process liquid and the optical window from the side of the process liquid and in the direction of the interface.

14 Claims, 3 Drawing Sheets

REFRACTOMETER

Figure 1:
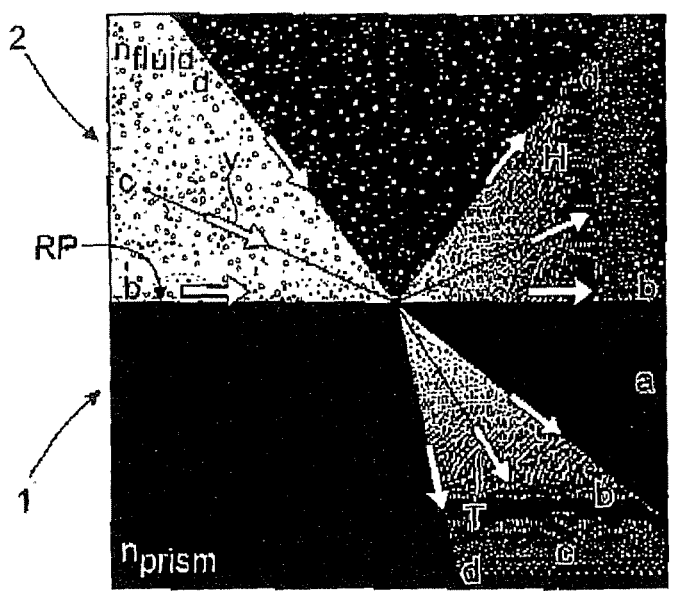

The invention relates to a refractometer comprising a light source, an optical window to be positioned in a process liquid, means for directing a beam of rays from the light source to an interface between the process liquid and the optical window and leading back part of the beam of rays refracted from the interface to the inside of the optical window, and means for observing an image formed in the above manner.

The operating principle of a refractometer has been known for over a hundred years already. At present, refractometers are used rather much in a plurality of different fields. As examples of the range of use of refractometers can be mentioned food industry, wood-processing industry, chemical industry and researches of different kind in general, in which a refractometer is used for measuring concentrations.

At present, the operation of widely used process refractometers is based on measurement of the critical angle of total reflection at the interface between the optical window and the liquid to be measured.

The operating principle of the above-mentioned process refractometers can be described generally as follows. A beam of rays from a light source is directed through an optical window to the interface between the optical window and a process liquid. Part of the beam of rays is reflected from the liquid entirely, part of it is absorbed partly into the liquid. This causes an image, in which the location of a borderline between a light area and a dark area depends on the critical angle of the total reflection and thus on the refractive index of the process liquid. An essential feature of refractometer measurement consists in analyzing an image created by light reflection. The purpose of such an image analysis is to find the critical angle of the total reflection, i.e. the borderline at which the light area of the image created in the above manner turns into a dark area.

Examples of the above-mentioned process refractometers include solutions described in Finnish Patents 108259 and 113566.

The operating principle of the above-mentioned known refractometers is good, because light to be applied to a measurement signal does not pass through the process liquid, and thus the color, particles and bubbles of the process liquid do not affect the measurement. A drawback is the inaccuracy of the critical angle, because in the optical image the borderline between light and shadow is not vertical, and thus the steepest point has been sought mathematically.

Another principle used in refractometer measurements is known from laboratory refractometers. According to this principle, light comes from the side of the liquid to be measured to the interface between the liquid and the optical window, part of the light being reflected from the interface to the inside of the optical window. A sample to be measured in the measurement is placed onto the surface of the optical window in such a manner that the sample is between the surface of the optical window and a ground glass above the surface. The light is led via the ground glass to the sample.

A drawback of the solution described above is that in practice it is suitable as such for laboratory uses only, because it is difficult to position a sensitive light source to demanding process conditions. The basic principle of the solution, i.e. the refraction of light to the inside of the optical window, is advantageous as such, because the borderline between light and shadow in the optical image is clearly steeper than in the solutions based on measurement of the critical angle of total reflection.

It is an object of the invention to provide a refractometer by which the prior art drawbacks can be eliminated so that the prior art advantages may also be utilized in difficult practical conditions, such as in difficult process conditions. This is achieved by means of a refractometer according to the invention. The refractometer of the invention is characterized in that the beam of rays from the light source is directed to the interface between the process liquid and the optical window from the side of the process liquid and in the direction of the interface.

An advantage of the solution of the invention is above all that the invention allows that the basic principle of the measurement previously known per se can also be applied in process conditions. Another advantage of the invention is the simplicity of the solution, which makes the implementation and use of the invention advantageous. The invention also provides the advantage that the basic principle of the invention may preferably be modified in various ways, i.e. the invention may preferably be modified according to requirements of each specific situation.

Figure 2:
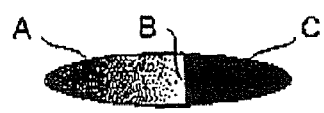
Figure 3:
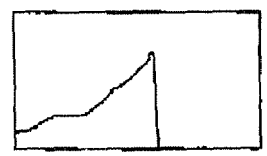
Figure 4:
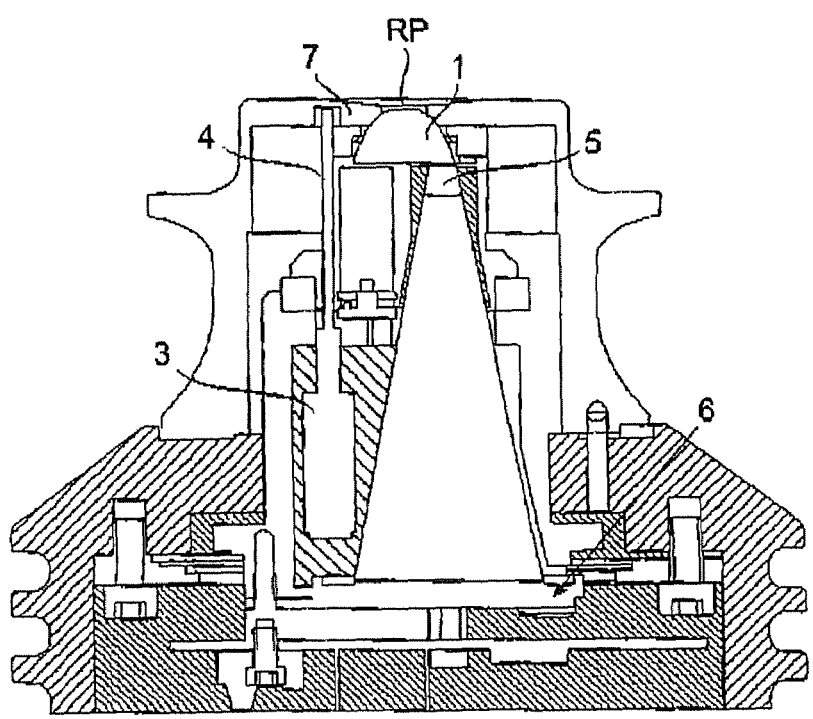
Figure 5:
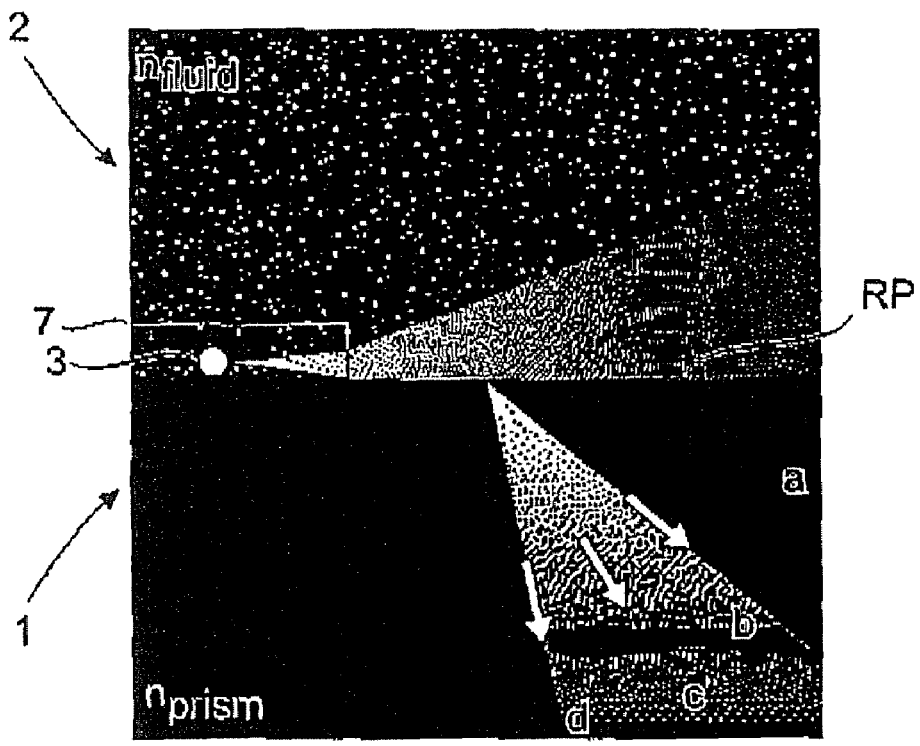
Figure 6:
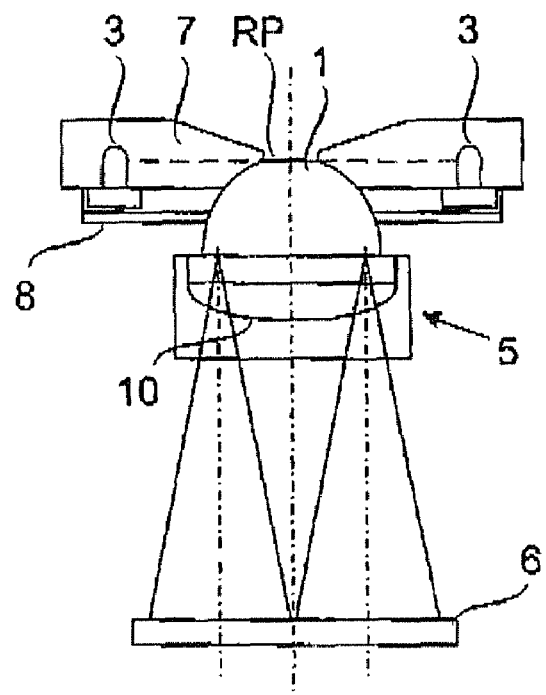
Figure 7:
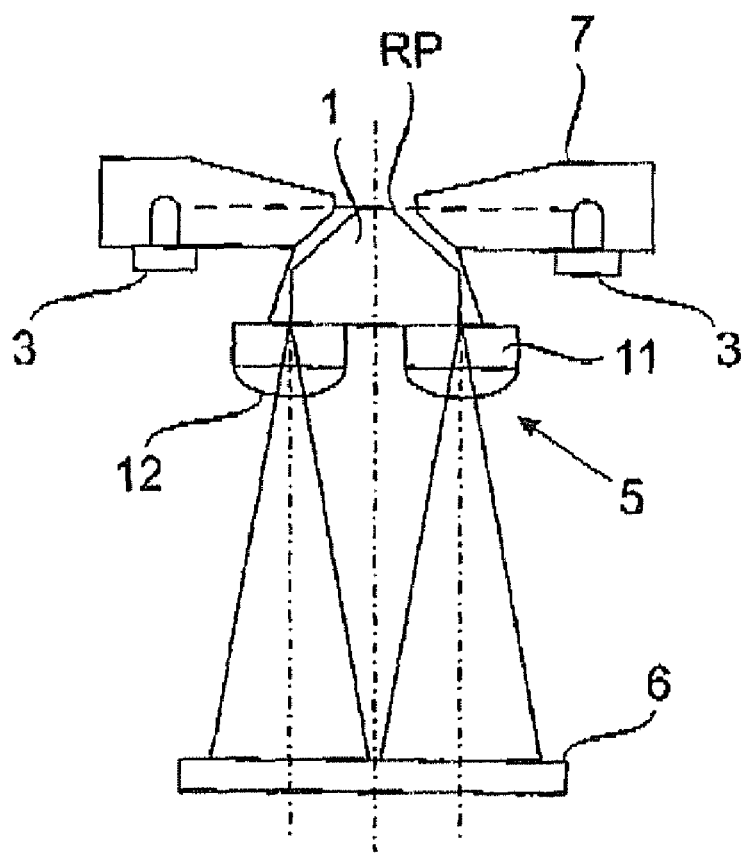
Figure 8:
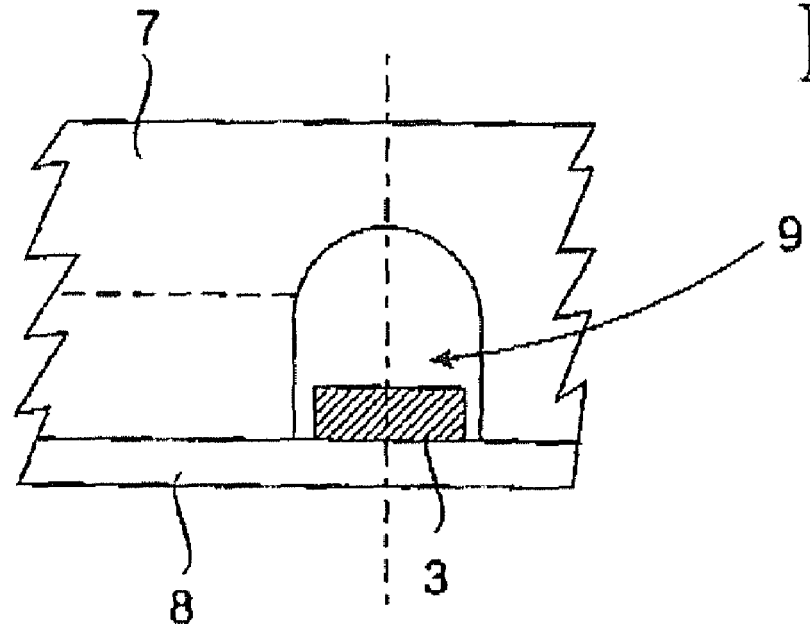

The invention will be described in greater detail by means of an example illustrated in the attached drawing, in which FIG. 1 illustrates the principle of a refractometer based on measurement of the angle of refraction, FIG. 2 illustrates an optical image, which forms when light is refracted to the inside of an optical window, as shown in FIG. 1, FIG. 3 illustrates a curve showing how light is distributed in the image of FIG. 2, FIG. 4 illustrates a principled side view of a refractometer of the invention, FIG. 5 illustrates the operating principle of the refractometer of FIG. 4, FIG. 6 illustrates a principled side view of a second embodiment of the refractometer of the invention, FIG. 7 illustrates a principled side view of a third embodiment of the refractometer of the invention, and FIG. 8 illustrates a detail of the embodiments of FIGS. 6 and 7 on a larger scale in a principled manner.

FIG. 1 shows the basic principle of a refractometer based on measurement of the angle of refraction. An optical window, which may be a prism, for instance, is denoted by a reference number 1. A liquid to be measured, which in this invention is a process liquid, is denoted by a reference number 2. The interface between the process liquid and the optical window is denoted by a reference RP in FIG. 1.

Light is led to the interface RP via the liquid 2 to be measured, as shown in FIG. 1 by arrows V. Part of the light that has arrived at the interface is reflected back from the interface to the liquid to be measured. This part of the light is denoted by arrows H in FIG. 1. Part of the light that has arrived at the interface is refracted to the inside of the optical window. This part is denoted by arrows T in FIG. 1. The above phenomenon causes an image, which is shown in FIG. 2. The location of a borderline C between a light area A and a dark area B depends on the refractive index of the liquid to be measured. FIG. 3 shows a curve illustrating the distribution of light in the image shown in FIG. 2. As can be seen from FIG. 3, the borderline between the light and dark areas is very steep, and thus the location of the borderline C between the light area and the dark area may be determined simpler than in refractometers based on measurement of the critical angle of total reflection, which have to use mathematical means as help, as was stated above.

FIG. 4 illustrates a principled side view of a refractometer of the invention. The refractometer shown in FIG. 1 comprises a light source 3 arranged in a frame structure and an optical window 1 to be positioned in a process liquid. The refractometer also comprises means 4 for directing a beam of rays from the light source to the interface between the process liquid and the optical window, and means 5 for leading back part of the beam of rays refracted from the interface to the inside of the optical window, and further means 6 for observing the image formed in the above manner. The means 4 for directing the beam of rays from the light source 3 onwards may comprise optical fibers, mirror elements or other similar elements, for instance. The means 5 for leading the light refracted to the inside of the optical window may comprise, for example, lens elements, optical fibers and other similar elements. The means 6 for observing the image may comprise a light detector, for instance.

The refractometer according to FIG. 4 is intended to be used in such a manner that during measurement, the optical window is in contact with the liquid to be measured, such as the process liquid. Thus, between the optical window 1 and the process liquid there is provided an interface RP where the light from the light source 3 is refracted according to the basic principle shown in FIG. 1.

According to the essential idea of the invention, the beam of rays from the light source 3 is led to the interface RP between the process liquid and the optical window in the direction of the interface. The above-mentioned essential basic idea of the invention is illustrated in FIG. 5 in a principled manner. The application according to FIG. 4 functions according to the principle of FIG. 5. In the application of FIG. 4, the light source 3 is arranged inside the frame structure of the refractometer, and light is led next to the optical window by using the means 4, and it is led from the side of the process liquid to the interface RP from the side of the optical window in the manner shown in FIG. 5. It is obvious that the light source 3 may also be positioned in such a manner that it is directly on the side of the optical window 1. The means 4 are arranged in such a manner that the liquid to be measured is not prevented from arriving at the optical window, e.g. so that the optical window 1 is not located in a very deep recess, which allows the process liquid to be measured to arrive freely at the optical window.

As shown above in FIGS. 4 and 5, the light source is positioned outside the process inside a measuring device. In the embodiment of FIG. 4, light is led to a ring element 7 made of an optical material. The ring element 7 is arranged to surround the optical window 1, as shown in FIG. 4. During the measurement, the ring element 7 is in contact with the process liquid. The ring element 7 made of an optical material is arranged to direct the light to the interface RP as rays parallel to the interface. The ring element 7 also acts as a casing material and mechanical part of the refractometer. The material of the ring element 7 may consist in sapphire, for instance, in which case the device may be used for measurements of the solid-state industry, where metals are not to be used on process surfaces. The ring element 7 may also be shaped in such a manner that it helps to keep the optical window 1 clean by means of process liquid flow and facilitates the change of the sample on the surface of the optical window.

In the embodiment of FIGS. 4 and 5, one light source 3 is used. However, this is not the only feasible embodiment of the invention. FIG. 6 illustrates a second embodiment of the invention, using two light sources 3. In this embodiment the light sources are LED components positioned in the ring element 7 made of an optical material. The LED components are attached to a circuit board 8 and arranged in holes 9 in the ring element 7 made of an optical material. The above-mentioned details are clearly shown in FIG. 8. The bottoms of the holes 9 may be conical or spherical surfaces. The conical or spherical surfaces may be polished or unpolished surfaces.

In the embodiment of FIG. 6, the means 5 for leading the light refracted to the inside of the optical window comprise a lens element 10. In this embodiment the lens element 10 is arranged to provide an integral optical component together with the optical window 1. The lens element 10 may be glued onto the optical window 1, or the lens element and the optical window 1 may be manufactured as an integral piece. In this way, one integral optical element is provided, which is not difficult to install and does not cause difficulties as a result of angle changes.

In the embodiment of FIG. 6, the ring element 7 made of an optical material is used for bidirectional light exposure by joining two light sources 3 to the ring element. Thus, a differential image is created at a light detector 6, which may be referred to as a differential refractometer. The measurement signal of the differential refractometer is the difference of two critical-angle images refracted at the optical window, whereby not the angle between the optical window and the light detector is critical but only the distance.

There may also be more than two light sources. The light sources may also be light sources that radiate at different wavelengths.

FIG. 7 illustrates a third example of the invention. In the example of FIG. 7 there are two lens elements 11, 12, instead of one lens element 10 shown in FIG. 6.

The above examples are not intended to restrict the invention in any way, but the invention may be modified freely within the scope of the claims. Thus, it is obvious that the refractometer according to the invention or the parts thereof need not necessarily be exactly similar to those shown in the figures, but other solutions are also feasible.

The invention claimed is:

1. A refractometer comprising a light source, an optical window to be positioned in a process liquid, means for directing a beam of rays from the light source to an interface (RP) between the process liquid and the optical window and leading back part of the beam of rays refracted from the interface to the inside of the optical window, and means for observing an image formed in the above manner, whereby the beam of rays from the light source is directed to the interface (RP) between the process liquid and the optical window from the side of the process liquid and in the direction of the interface and whereby the refractometer also comprises a ring element surrounding the optical window and made of an optical material, wherein the beam of rays from the light source is led to the ring element made of an optical material, the ring element being arranged to lead the beam of rays to the interface (RP) between the process liquid and the optical window.

2. A refractometer as claimed in claim 1, wherein there is one light source.

3. A refractometer as claimed in claim 1, wherein there are two light sources.

4. A refractometer as claimed in claim 1, wherein there are more than two light sources.

5. A refractometer as claimed in claim 2, wherein the light sources are LED components.

6. A refractometer as claimed in claim 5, wherein the LED components are attached to a circuit board and arranged in holes in the ring element made of an optical material.

7. A refractometer as claimed in claim 6, wherein the bottoms of the holes in the ring element made of an optical material may be conical or spherical surfaces.

8. A refractometer as claimed in claim 3, wherein the light sources are arranged to radiate light at different wavelengths.

9. A refractometer as claimed in claim 1, wherein the means for leading back part of the beam of rays refracted to the inside of the optical window comprise one or more lens elements arranged to provide an integral optical component together with the optical window.

10. A refractometer as claimed in claim 9, wherein the lens element/s is/are glued onto the optical window.

11. A refractometer as claimed in claim 9, wherein the lens element/s form/s an integral part of the optical window.

12. A refractometer as claimed in claim 3, wherein the light sources are LED components.

13. A refractometer as claimed in claim 4, wherein the light sources are LED components.

14. A refractometer as claimed in claim 4, wherein the light sources are arranged to radiate light at different wavelengths.

* * * * *